United States Patent
Aarestad et al.

(10) Patent No.: US 10,709,358 B2
(45) Date of Patent: Jul. 14, 2020

(54) SIZING DEVICE, AND METHODS OF MANUFACTURE AND USE THEREOF

(71) Applicant: SOMMETRICS, INC., San Diego, CA (US)

(72) Inventors: Jerome K. Aarestad, Escondido, CA (US); David M. Giuntoli, San Diego, CA (US)

(73) Assignee: SOMMETRICS, INC., Vista, CA (US)

( * ) Notice: Subject to any disclaimer, the term of this patent is extended or adjusted under 35 U.S.C. 154(b) by 379 days.

(21) Appl. No.: 15/739,741

(22) PCT Filed: Jun. 24, 2016

(86) PCT No.: PCT/US2016/039418
§ 371 (c)(1),
(2) Date: Dec. 24, 2017

(87) PCT Pub. No.: WO2016/210367
PCT Pub. Date: Dec. 29, 2016

(65) Prior Publication Data
US 2018/0177435 A1 Jun. 28, 2018

Related U.S. Application Data

(60) Provisional application No. 62/184,809, filed on Jun. 25, 2015.

(51) Int. Cl.
*A61B 5/107* (2006.01)
*A61F 5/055* (2006.01)
(Continued)

(52) U.S. Cl.
CPC .......... *A61B 5/1077* (2013.01); *A61B 5/4851* (2013.01); *A61F 5/055* (2013.01);
(Continued)

(58) Field of Classification Search
CPC ... A61B 17/1668; A61B 17/175; A61B 17/86; A61B 17/164; A61B 17/1666;
(Continued)

(56) References Cited

U.S. PATENT DOCUMENTS 5,584,125 A * 12/1996 Prete ..................... A61M 16/06
33/501.45
5,845,638 A * 12/1998 Pretel .................. A61B 5/1071
600/595

(Continued)

OTHER PUBLICATIONS

International Search Report and Written Opinion issued in PCT/US2016/039418 dated Sep. 14, 2016 (9 pages).

*Primary Examiner* — Yaritza Guadalupe-McCall
(74) *Attorney, Agent, or Firm* — Acuity Law Group, PC; Michael A. Whittaker (57) ABSTRACT

The present invention relates to a sizing device and includes a sizing frame and frame handle for the evaluation of the fitting of a therapy device to a patient. The sizing frame corresponds to the contact region of a therapy device and the inner area of the sizing frame corresponds to the target therapy area. The sizing device is designed to provide a visual indication of correct or incorrect fit of the sizing device and the subsequent corresponding therapy device.

19 Claims, 5 Drawing Sheets

(51) Int. Cl.
*A61F 5/56* (2006.01)
*A61B 5/00* (2006.01)
*A61H 9/00* (2006.01)
*B29C 49/06* (2006.01)
*A61B 90/00* (2016.01)

(52) U.S. Cl.
CPC ............ *A61F 5/56* (2013.01); *A61H 9/0057* (2013.01); *B29C 49/06* (2013.01); *A61B 5/1071* (2013.01); *A61B 5/1072* (2013.01); *A61B 5/6822* (2013.01); *A61B 2090/061* (2016.02); *A61H 2201/1207* (2013.01); *A61H 2201/1604* (2013.01); *A61H 2201/165* (2013.01); *A61H 2201/168* (2013.01); *A61H 2201/1645* (2013.01); *A61H 2201/1647* (2013.01); *A61H 2201/5007* (2013.01); *A61H 2201/5043* (2013.01); *A61H 2205/022* (2013.01); *A61H 2205/04* (2013.01)

(58) Field of Classification Search
CPC ............ A61B 17/1717; A61B 17/1721; A61B 17/7283; A61B 2017/924; A61B 17/1664; A61B 17/1684; A61B 17/7266

USPC .................................................. 33/511, 512
See application file for complete search history.

(56) References Cited

U.S. PATENT DOCUMENTS

| | | | |
|---|---|---|---|
| 6,178,652 B1* | 1/2001 | Foster | A61B 5/107 33/511 |
| 7,182,082 B2 | 2/2007 | Hoffrichter | |
| D650,905 S * | 12/2011 | Plascott | D24/140 |
| 8,122,891 B2 | 2/2012 | Kimani | |
| 2003/0167018 A1 | 9/2003 | Wyckoff | |
| 2004/0093751 A1* | 5/2004 | Tranas | A63B 23/0244 33/512 |
| 2006/0266369 A1 | 11/2006 | Atkinson et al. | |
| 2011/0066086 A1 | 3/2011 | Aarestad et al. | |
| 2014/0373374 A1* | 12/2014 | Znamenskiy | A61B 5/1077 33/512 |
| 2015/0007439 A1* | 1/2015 | Todd | A61B 5/1075 33/512 |
| 2016/0067436 A1* | 3/2016 | Grashow | A61B 5/1077 33/512 |
| 2018/0177435 A1* | 6/2018 | Aarestad | A61B 5/1077 |

* cited by examiner

SIZING DEVICE, AND METHODS OF MANUFACTURE AND USE THEREOF

The present invention is filed under 35 U.S.C. § 371 as the United States national phase of International Application No. PCT/US2016/039418, filed Jun. 24, 2016, which designated the United States and claims priority from U.S. Provisional Application No. 62/184,809, filed Jun. 25, 2015, each of which is hereby incorporated by reference in its entirety, including all tables, figures and claims.

BACKGROUND OF THE INVENTION

The following discussion of the background of the invention is merely provided to aid the reader in understanding the invention and is not admitted to describe or constitute prior art to the present invention.

U.S. Pat. Nos. 5,343,878, 7,182,082, and 7,762,263 describe various devices which purport to utilize external application of negative pressure upon the external neck surface of patients. A therapeutic appliance is typically provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage. In certain embodiments, these appliances can provide a chamber (e.g., a hollow space filled with air molecules) lying between the surface and the throat. The therapy appliance is operably connected to an air pump which is configured to produce a partial vacuum in this chamber.

BRIEF DESCRIPTION OF THE INVENTION

It is an object of the invention to provide methods and apparatuses for the fitting of therapy devices for the administration of negative pressure upon the external neck surface of patients. To ensure the therapy area is correctly targeted and to provide a good seal over the therapy area, the present invention can provide a customizable fit between the device and the therapy area of an individual patient. As it is undesirable to waste an expensive medical device for this sizing procedure, and because such devices in general are designed such that they obscure the therapy area, the devices of the present invention provide for a system that is reusable and that provides the caregiver with simple visual cues regarding an appropriate fit. The result is improved therapeutic efficacy and reduced vacuum leakage.

In a first aspect, the invention provides a sizing system comprising one or more sizing frames configured to be placed on a surface of an individual to aid in the selection of an appropriately sized therapy device for positioning on the external anatomy of the individual.

A sizing frame of the invention is preferably configured to conform to the external area of the neck approximately corresponding to the anterior triangle of the neck. Most preferably, these devices comprise (i) a first curved element configured to approximately conform to an individual from approximately the gonion on one side of the mandibular body, across the mental protuberance, and to the opposite gonion of the mandibular body, (ii) a second curved element configured to approximately conform to an individual from approximately the gonion on one side of the mandibular body to a position on the neck at the level of the thyroid cartilage, and to the opposite gonion of the mandibular body, and (iii) a handle spanning the region between the first curved element and the second curved element. In most preferred embodiments, the first curved element, the second curved element, and handle are made as a unitary device.

The remainder of the internal area lying between the first curved element, the second curved element, and handle is preferably either unoccupied or made of a transparent material, such that the fit of the first curved element and the second curved element to the individual's anatomy can be visualized from a position of what will be internal to the desired therapy device for which the sizing device is being utilized.

In certain embodiments, the sizing frame is formed of a transparent material, such that the fit of the first curved element and the second curved element to the features of the individual's anatomy corresponding to the therapy device contact area can be observed for approximation of the best fitting therapy device for which the sizing device is being utilized.

In certain embodiments, the sizing frame is provided as a system comprising a plurality of individual sizing frames of different shapes and/or sizes, each of which provide surfaces configured to fit on a predetermined area of a subject. Each sizing frame in the system is configured to vary in size to provide a visual indication of correct or incorrect fit of a therapy device. By selecting a "best fitting" sizing frame from among the plurality of available frames, an individual is assigned a corresponding therapy device which best approximates the individual's anatomy.

In certain embodiments, one or more sizing identifiers may be present on the sizing frame such as on the first curved element, the second curved element, and/or the frame handle element. The sizing identifier can provide a means to ascertain the size of the frame in use and corresponding therapy device. As used herein a sizing identifier may include any feature used to identify the frame as corresponding to a particular size for example, color, texture, text or symbols. These identifiers, for example, may identify a frame as being small, medium or large; or corresponding to certain known anatomical groupings as defined below.

In certain embodiments, one or more orientation identifiers may be present on the sizing device including the sizing frame element, frame handle element or both which provides a means to ascertain the correct orientation of the sizing frame in use. As used herein a orientation identifier may include any feature used to identify the orientation, top bottom, left, right etc. of the sizing device for example, color, texture, text or symbols.

In certain embodiments, one or more tabs or handles are present on the sizing frame which provides one or more points to hold the sizing device during application of the sizing frame on the patient. In preferred embodiments, one or more of these tabs is designed to provide minimal visual obstruction to ensure the best possible observation of therapy area.

The sizing device may be made of a generally rigid material. The term "generally rigid" as used herein refers to a material which is sufficiently rigid to maintain the integrity of the particular element in question. The skilled artisan will understand that a number of polymers may be used including thermoplastics, some thermosets, and elastomers. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

The sizing frame element and the sizing frame handle element may be formed using a number of methods known to those of skill in the art, including but not limited to injection molding, machining, etching, 3D printing, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold—in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

The term "sizing frame" refers to a discreet element of the sizing device which comprises a shaped frame designed to have a contact surface that corresponds to the contact surface of a therapy device. The area covered by the sizing frame element corresponds approximately to the contact surface of the therapy device. The area contained within the inner edges of the frame correspond to the approximate therapy area of the patient and upon placement of the frame on the patient it is visually apparent a correct or incorrect fit can be obtained with a therapy device of a size corresponding to visual cues and or measurements obtained from the sizing frame. This depends on how the sizing frame elements overlap the mandible, butt up near the ears and conform to the patient's neck surface when the lower curved element of the sizing frame is located on the patient's neck, as described further below.

The term, "visual cues" refers to observables that aid in the fitting, aligning and or measuring with the sizing device. Visual cues may include (i) features of the individual for example the chin, mandible, ear, and or gonion, (ii) elements of the sizing device for example sizing frame elements, chin cup, frame handle, and or markings on the sizing device for example a sizing grid. This list is not meant to be limiting, and visual cues may be performed by features or elements other than those listed above.

The term "frame handle" refers to a discrete element of the sizing device which comprises a tab(s) or handle(s) a user can hold during application of the sizing device. The handle is positioned at a location opposite to the area designed to contact the patient and may also provide a structural element to the sizing frame in the form of rigidity of the sizing frame.

The term "chamber gauge" refers to a discreet element of the sizing device which comprises a shaped frame, designed a mimic the exterior features of a corresponding therapy device. The sizing element may be designed such that either inner edges or outer edges correspond to features of the therapy device and upon placement of the sizing device on the patient it is visually apparent if a correct or incorrect fit can be obtained with a particular sized frame and subsequently, therapy device. In certain aspects the chamber sizing feature may be integrated into the frame handle element.

The sizing frame and or frame handle(s) may also participate in other functions regarding the identification of the size of a particular frame. For example the sizing frame and or one or more handles may contain features that identify the size or function of the sizing device. Identifying features may include labels, color, text, bumps, recesses or a combination thereof. This list is again not meant to be limiting, and these aspects may be performed by elements of the device other than the features(s) as described hereinafter.

The sizing frame may contain features to ensure consistent fitting of the sizing device. By way of example, the sizing frame element may contain a chin cup. The term "chin cup" refers to a discreet feature of the sizing frame which comprises a recess for accommodating the chin feature of a patient's face. During application of the sizing device, the chin cup provides a consistent point of reference for the sizing frame. The shape of the chin cup may vary to allow for anatomical variation in patients for example, prognathia, retrognathia or macrogenia and correspond to therapy devices designed taking in to consideration these types of variations. The sizing frame considers, both at once, the patient's anatomical dimensions and posture for a proper therapy device fitting. Using the chin and lower point on the next as contact surfaces, the sizing frame determines if the critical sizing reference points, mandible, gonion and lower ear, are within the functional range for a given sizing-frame size and subsequent therapy device.

As defined herein a "consistent point of reference" or "critical sizing reference point" refers to a location to which the sizing device is consistently placed upon and or observed at where conditions associated with correct placement of the sizing frame element can be evaluated. This includes, but is not limited to, measurements, proper orientation and or proper mating of the sizing frame element to the desired features of the patient.

A consistent point of reference for example can be the axis of the chin, lower edge of the mandible and or the gonion. As used herein the axis of the chin is the vertical bisection point of the chin feature on an individual. Further as used herein the gonion is the point on the mandible located at the apex of the maximum curvature on the exterior angle of the mandible. The axis of the chin and the location of the gonion may be utilized as length and angle reference points upon fitting of a sizing device and observation of the alignment of a sizing grid. The sizing frame may also contain features to grade the fit and aid in the selection of a therapy device. By way of example, the sizing frame element may contain a sizing grade system that may be in the form of a grid to provide a classification of size. During application of the sizing device, a measurement from the axis of the chin cup to the marking on the gonion and the vertical components of the grid provide a length value of the mandible of a patient and similarly alignment of the horizontal components of the grid and the gonion provide a value to the head to neck angular relationship is relative to the.

As used herein, "structure support area" is the region on the face of a patient corresponding to the mandible where the upper area of a sizing frame is designed to make contact with the patient beginning at the chin cup extending toward the ear. Further, "mandible overlap" corresponds to the mandible structural support area exposed in the interior of the sizing frame below the inner edge of the sizing frame.

The sizing device may be fitted to the patient with the goal of maximizing an effective therapy area. As used herein "effective therapy area" is the area of the neck corresponding to the exterior surface of the upper airway.

As used herein the "mandible overlap dimension" is the distance between the inner edge of the upper region of the sizing frame extending over the mandible to the lower mandible of the patient.

As used herein the "ear clearance dimension" is the distance between the lower portion of the ear and the closest outer edge of the sizing frame.

As used herein "depth of chin" refers to the distance between the chin and gonion for example, individuals with retrognathism or prognathism will have a smaller or larger depth of chin respectively.

In a related aspect, the present invention relates to methods for selection of an appropriately sized therapy device for positioning on the external anatomy of the individual. These methods comprise placing one or more of the sizing frames of the present invention onto an external portion of the individual corresponding to the desired location for the therapy device, and determining whether the sizing frame provides a sufficiently good fit to the individual's anatomy.

In a similar aspect, present invention relates to methods for selection of an appropriately sized therapy device for positioning on the external anatomy of the individual. These methods comprise placing each of a plurality of the sizing frames of the present invention onto an external portion of the individual corresponding to the desired location for the therapy device, and determining which sizing frame of the plurality best corresponds to the individual's anatomy.

Optionally, the methods further comprise assigning a therapy device corresponding in size to a selected sizing frame to the individual and initiating therapy.

In preferred embodiments, the sizing frame used in these methods is preferably configured to conform to the external area of the neck approximately corresponding to the anterior triangle of the neck, and the therapy device assigned is configured for positioning on the individual at an external area of the neck approximately corresponding to the anterior triangle of the neck. Most preferably, the therapy initiated is external application of negative pressure upon the external neck surface for increasing patency of the airway. Such methods include treatment of conditions such as sleep apnea and snoring, or for medical interventions such as intubation or administration of gases. This list is not meant to be limiting.

The sizing device may be fitted to a patient while in a "nominal position". As used herein, the phrase "nominal position" refers to a neutral position where the spine is straight and the neck is open for example positioned in a seated position on a stool or chair with the back and shoulders straight and face parallel with a vertical surface. A nominal position may also be achieved while standing or laying down.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

In the present invention a sizing device is designed to be placed on a patient to aid in the selection of an appropriately sized therapy device, including the placement and removal of a series of sizing frames that are designed to mimic the shape of a therapy device and therapy area.

In particular, the therapy device referred to herein relates but is not limited to an external therapy appliance for relieving upper airway obstruction. U.S. patent application Ser. Nos. 12/002,515, 12/993,311 and 13/881,836 which are hereby incorporated by reference in their entirety including all tables, figures and claims, describes a therapy appliance for relieving airway obstruction. As described therein, a device is configured to fit under the chin of a user at an external location corresponding to the soft tissues overlying the upper respiratory passages of the neck.

Figure 1:
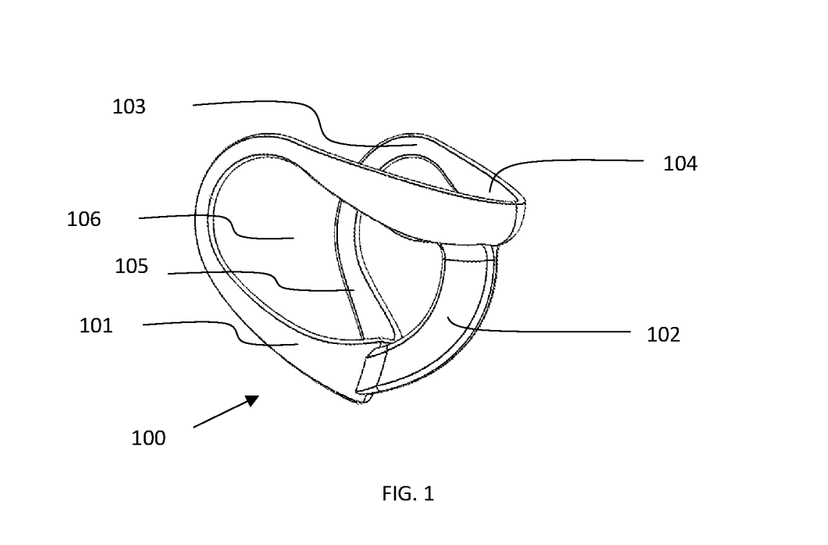
FIG. 1 is an exterior view of an illustrative embodiment of the sizing device 100, with the outer surface of the sizing frame 101 and sizing frame handle/chamber gauge 102, also shown is the contact surface 103, chin cup 104, neck/lower contact surface 105, open area interior of the frame to encompass the therapy area 106.
Figure 7:
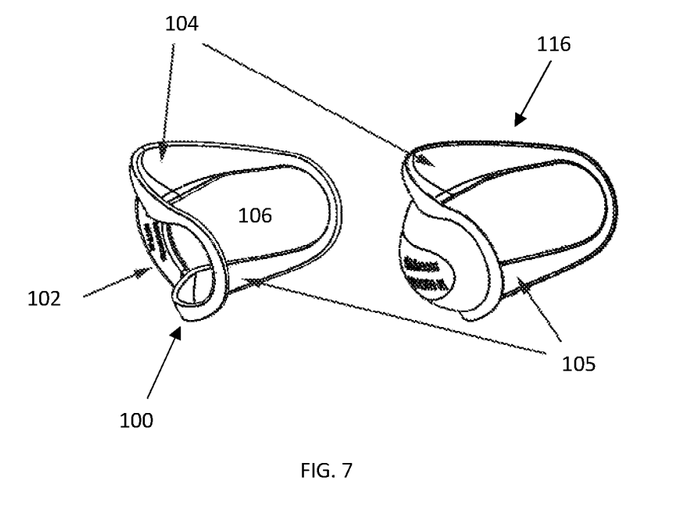
FIG. 7 is a an illustrative embodiment of the sizing device 100, with corresponding therapy device 116, including corresponding chin cup(s) 104, sizing frame handle/chamber gauge 102, corresponding neck/lower contact surface(s) 105, also shown is the open area interior of the frame corresponding to the therapy area 106.

The sizing device of the present invention comprises a structural member that provides a sizing frame 100 designed to mimic the contact area of a therapy device 116 used to create a vacuum between an inner surface of the appliance and the skin of the throat 108, where the structure of the sizing device is sufficiently rigid to withstand multiple fitting sessions.

Figure 3:
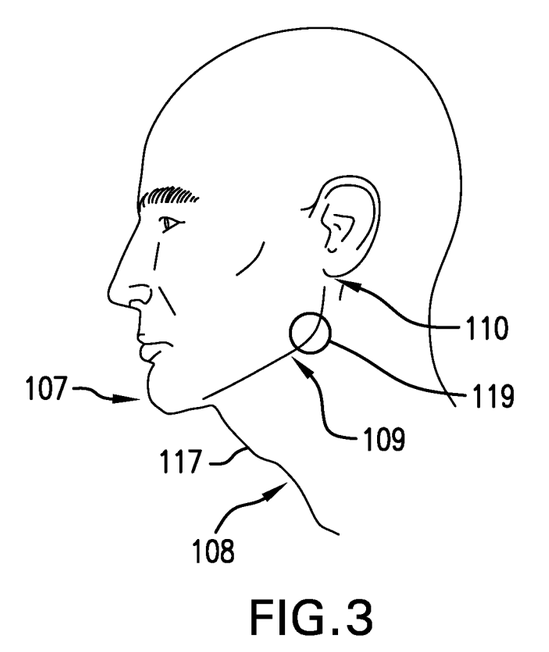
FIG. 3 is a side view of an illustrative embodiment of a patient, identifying the mental protuberance (i.e., the chin) 107, neck 108, lower mandible 109, lower ear 110 and laryngeal prominence 117 and gonion 119.

The sizing device 100 may be made of any compatible material both solid and or translucent in color and generally rigid. In an embodiment of the invention the sizing device 100 that is translucent either in whole or part may allow a user to observe facial features during a fitting session, for example but not limited to, the chin 107, neck 108, mandible 109, lower ear 110, therapy area 111, laryngeal prominence 117 and or gonion 119.

Further, the sizing 100 device may be formed, molded, or fabricated from any material or combination of materials. Non-limiting examples of such materials suitable for constructing the therapy appliance include plastics, metals, natural fabrics, synthetic fabrics, and the like. The sizing device 100 may also be constructed from a material having resilient memory such as silicone, rubber, or urethane.

In an embodiment of the present invention the sizing device 100 contains an outer surface 101 to visualize the footprint of a corresponding therapy device, a chin cup 104 to provide a consistent axial placement point on a patient, a mandible/upper interior contact surface 103 to locate on the mandible/structure support area 112 and determine mandible overlap dimension 114, a neck/lower interior contact surface 105, a sizing frame handle/chamber gauge 102 that allows for handling point and is shaped to mimic and gauge the clearance between the therapy area 111 and chamber of a corresponding therapy device 116 for the determination of the correct depth and volume of a corresponding therapy device 116, and an interior open area 106 of the sizing frame to encompass and visualize the therapy area 111. These features, all or in part, may be designed to aid in the rapid application and removal of the sizing device 100 and subsequent rapid visualization and selection of a corresponding therapy device 116.

Figure 8:
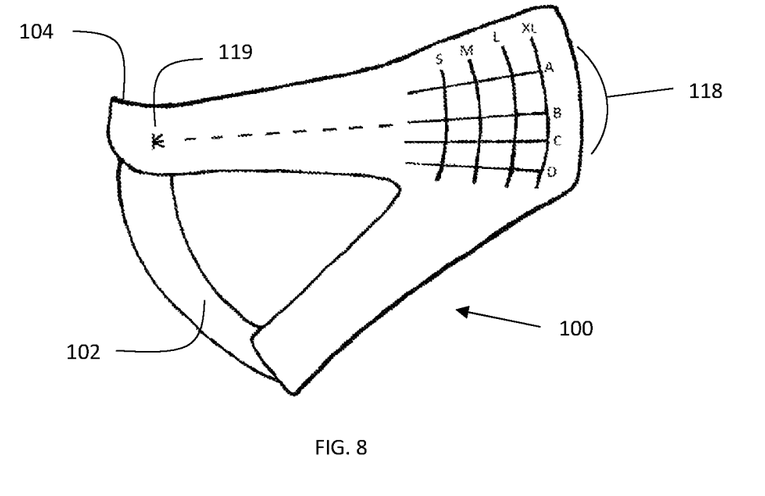
FIG. 8 is a side view of an illustrative embodiment of the sizing device 100, sizing frame handle/chamber gauge 102, chin cup 104, sizing grid 118 and sizing grid origin 119.
Figure 9:
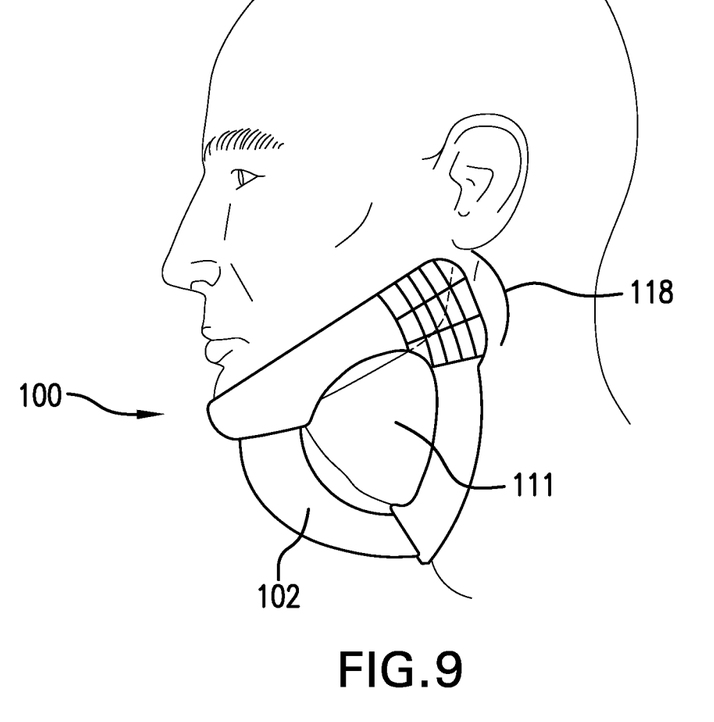
FIG. 9 is a side view of an illustrative embodiment the sizing frame 100 placed on a patient, including the frame handle/chamber gauge 102, therapy area 111 and sizing grids 118.

In an embodiment of the present invention, the sizing device 100 may be a single sizing frame molded to span all device sizes or multiple sizing frames molded to span a range of device sizes and containing a sizing grid feature 118. The sizing grid feature 118 may utilize facial features as a consistent point of reference to aid in the selection of an appropriately sized therapeutic device. These sizing frames are clear or translucent to allow visualization of facial features through the sizing frame. The sizing grid feature 118 may be made of vertical and horizontal lines with the vertical lines corresponding to the length of a corresponding device and the horizontal lines corresponding the size of corresponding device. The sizing grid may also contain an origin 119 from which consistent measurements can be made. Measurements may include length, distance from origin to a vertical line of sizing grid and angle, the A length parameter may be achieved by measuring the distance from a known point on the chin to the gonion feature 119 of a patient by correct placement of the sizing device on a patient and observation of the alignment of the gonion feature 119 within the sizing grid 118. Further, an angle measurement may be achieved by observing the location of a horizontal line of the sizing grid 118 on the gonion feature 119 of the patient.

In an embodiment of the invention the sizing frame is designed to configure to a therapy area corresponding to the upper airway of a patient including but not limited to the chin 107, the mandible 109 and neck 108 regions. The relevant therapy area on the neck surrounds the unsupported upper airway and comprises the region above the trachea, below the chin/mandible and around the neck towards the ears. This is the region that when negative external pressure is applied is able to move outwards and pull out the walls of the underlying airway, expanding its caliber. The airway is constrained from moving at the back of the neck by the spinal column.

Figure 4:
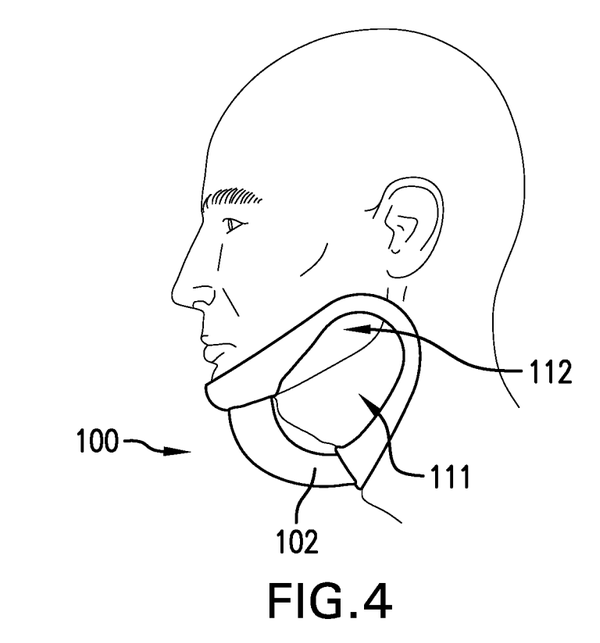
FIG. 4 is a side view of an illustrative embodiment of a patient with sizing device 100 applied, frame handle/chamber gauge 102, exposed structure support area 112 and effective therapy area 111.

The sizing frame may further be designed to locate, as a point of reference, on the chin 107 of a patient via a chin cup feature 104, ensuring consistent alignment of the frame(s) through multiple fittings. In general sizing frame, may extend over the upper airway, where the frame represents the contact surface 103, 105 of a therapy device and the area within the inner edges of the frame representing the therapy area 106, 111. The usage of the sizing device allows rapid size evaluation including visualization of the fit over the therapy area 111, fit over the mandible 112 and observation of pressure points.

Figure 6:
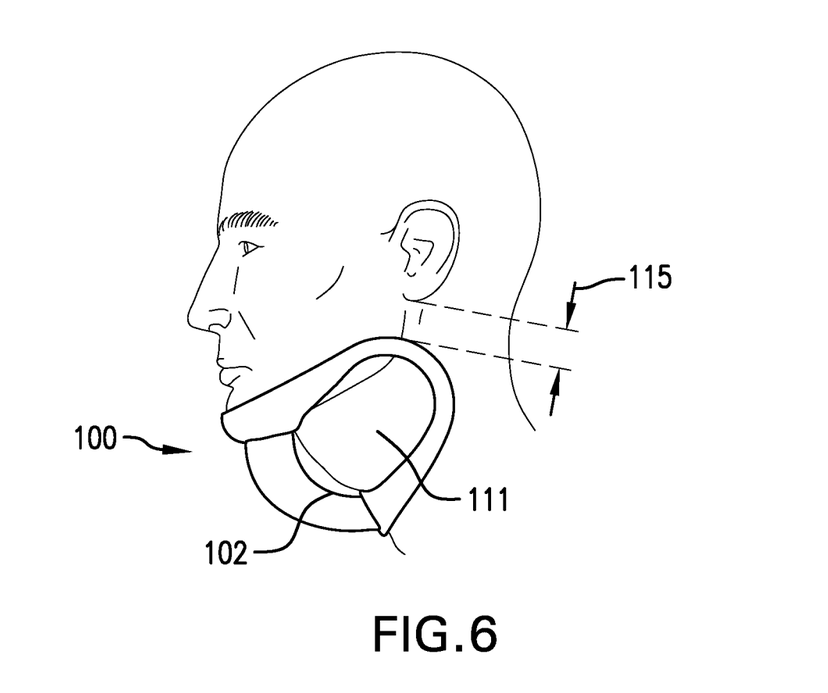
FIG. 6 is a side view of an illustrative embodiment the sizing frame 100 placed on a patient, including the frame handle/chamber gauge 102, therapy area 111 and identifying ear clearance dimension 115.

In an embodiment of the invention the sizing frame provides a visual guide for the rapid selection of an optimally sized therapy device. The vacuum chamber, configured to interface with the upper airway of a patient, is optimally sized when the structure support area 112 is minimized and the therapy area 111 is maximized by a device that locates on the chin 107 of the patient and makes contacts, with its upper contact surface 103, along the lower portion of the mandible 112 (structure support area) extending toward the ear 110 approaching at the most within about 1 cm of the ear and preferably no more than about 3.5 cm from the ear (ear clearance dimension 115) and traveling down the neck making contact with the lower neck with its lower contact surface 105 (second curved element).

Figure 2:
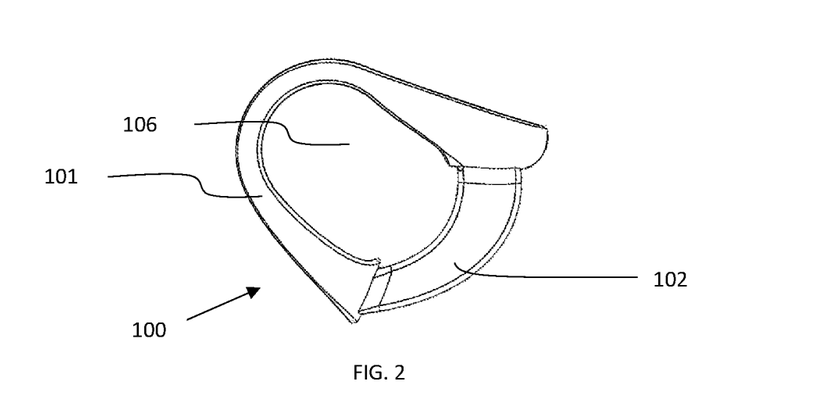
FIG. 2 is a side view of an illustrative embodiment of the sizing device 100, with the sizing frame 101 and frame handle/chamber gauge 102, also shown is the open area interior of the frame to encompass the therapy area 106.

In an embodiment of the invention the sizing frame 100 can provide several sizing parameters including but not limited to overall size of therapy devices, depth of chin, distance between the chin and ear, width of therapy device and distance between chin and lower neck. Further the frame handle 102 can be designed to integrate chamber depth parameters allowing evaluation and selection of a therapy device with a proper chamber size. For example a therapy device having a smaller chamber may not necessarily be compatible with patients having a probability of soft tissue interference and compatibility can be rapidly identified upon sizing frame placement on a patient. In an embodiment, if the soft tissue of the patient's neck is in close proximity to the inner edge of the sizing frame handle/chamber gauge a sizing frame representative of a deeper therapy device may be used for further sizing. In a preferred embodiment, the inner edge of the chamber gauge feature 102 of the sizing device is separated from the surface of the patient's skin corresponding to the therapy area by at least 1 cm.

In an embodiment of the invention a recommended fitting procedure would be as follows: patients are prepared for sizing by the removal of potential obstructions from the fontal regions of their neck including but not limited to clothing, loose earrings, and or long hair and placed in a nominal position with their back and shoulders straight and face parallel to a vertical wall. The gonion feature of the patient is marked. A sizing frame 100 is selected. The sizing frame(s) may be color coded or labeled in any manner as to identify size and distinguish varying sizing frames. In a preferred embodiment a sizing frame is chosen in approximate accordance with a patients chin type for example retrognathic or non-retrognathic.

The sizing frame 100 is positioned by grasping the sizing frame handle 102 and placing the sizing frame 100 on the patient with the axis of the chin cup 104 element locating on the axis of chin 107 of the patient. The sizing frame 100 is then rotated toward the neck 108 of the patient until the lower portion (second curved element) of the sizing frame 105 makes contact with the neck 108 of the patient with the edges of the sizing frame in close contact with the skin making the sizing frame correctly positioned and ready for observation and measurements. If the sizing frame 100 is found to make unfavorable contact with the laryngeal prominence 117 of the patient, a larger or smaller frame may be selected and fitting procedure repeated.

Figure 5:
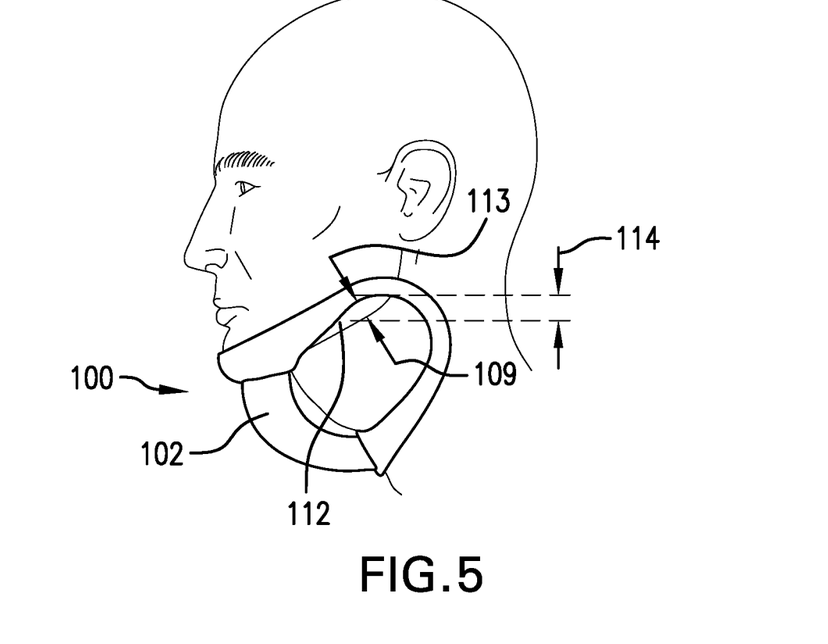
FIG. 5 is a side view of an illustrative embodiment the sizing frame 100 placed on a patient including the frame handle/chamber gauge 102, lower mandible of the patient 109, exposed structure support area 112, inside edge of the upper region of the sizing frame 113 and mandible overlap dimension 114

In a further embodiment of the invention fitting is continued by establishing the mandible overlap dimension 114 by measuring the distance between the lower mandible 109 to the inside edge of the sizing frame 113 or horizontal bar of the sizing grid 118. In a preferred embodiment of the invention, a correct mandible overlap 114 is achieved with a distance range of 0 to 1.5 cm. If the value between the mandible 109 to the inside edge of the sizing frame 113 is greater than 1.5 cm another sizing frame 100 should be selected and fitting repeated.

In a further embodiment of the invention fitting is continued by establishing the distance between the ear and the outer edge of the sizing frame or vertical bar of the sizing grid 118. The placement of an appropriately sized frame is achieved when the value of the distance between the ear and the outer edge of the sizing frame is between about 1 cm and about 3.5 cms. Further, if the value is less than about 1 cm the sizing frame 100 should be considered too large and the fitting procedure is repeated with a smaller sizing frame 100. Further still, if the value is great than about 3.5 cms, the sizing frame 100 should be considered too small and the fitting procedure is repeated with a larger sizing frame 100.

In a preferred embodiment the best fit is achieved when the effective therapy area 111 (the region of the neck overlying the upper airway) is maximized and the exposed structure support area 112 (the area above the mandible inside the sizing frame) is minimized. Upon selection of an appropriately sized sizing frame and verification of optimized fitting parameters, the prescription of a corresponding therapy device may be made.

In a preferred embodiment the best fit is further achieved when the effective therapy area 111 (the region of the neck overlying the upper airway) is maximized and the exposed structure support area 112 (the area above the mandible inside the sizing frame) is minimized. Prior to fitting of the device on the patient the gonion feature is marked and upon observation of the alignment of a sizing grid over the marked gonion feature of a patient a corresponding therapy device may be selected. A device is selected corresponding to the closest intersecting labels. For example if the gonion feature is observed through the sizing frame to locate with a vertical value of Y and a horizontal value of X, a device corresponding to those values is prescribed.

Structural embodiments of the apparatus may vary based on the size of the device and the description provided herein is a guide to the functional aspects and means.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims

The invention claimed is:

1. A sizing frame for determining the fit of a therapy device, the therapy device configured to mate to an individual at a position corresponding approximately to the anterior triangle of the neck of the individual to create an enclosed space for the administration of negative pressure upon the external neck surface of the individual, the sizing frame comprising:
 a mating surface configured to engage with a surface on the individual corresponding to the contact surface of the therapy device, the mating surface configured to permit visualization of the individual's skin surface from a position that will be internal to the enclosed space of the desired therapy device.

2. A sizing frame according to claim 1, wherein the sizing frame comprises (i) a first curved element configured to approximately conform to an individual from approximately the gonion on one side of the mandibular body, across the mental protuberance, and to the opposite gonion of the mandibular body, (ii) a second curved element configured to approximately conform to an individual from approximately the gonion on one side of the mandibular body to a position on the neck at the level of the thyroid cartilage, and to the opposite gonion of the mandibular body, and (iii) a handle spanning the region between the first curved element and the second curved element.

3. A sizing frame of claim 2, wherein the sizing frame contains one or more structural elements configured to receive a predetermined anatomical feature of the patient to ensure proper positioning of the sizing frame element on the individual.

4. A sizing frame of claim 3, wherein the structural element(s) comprise a recess to receive the chin of the individual.

5. A sizing frame according to claim 4 wherein the sizing frame further contains a tab extending outward from an outer surface of the sizing frame corresponding to the interface between the first and second curved elements.

6. A sizing frame according to claim 5, wherein a surface of the handle is configured mimic the position of an internal surface of a therapy device.

7. A sizing frame according to claim 1, wherein an element of the frame indicates a corresponding therapy device.

8. A sizing frame according to claim 7, wherein the element is a color.

9. A sizing frame according to claim 7, wherein the element is alphanumeric.

10. A sizing frame according to claim 7, wherein the element is an encoded label.

11. A sizing frame according to claim 1, wherein the at least a portion of the frame material is sufficiently translucent to observe the facial features of the individual through the frame.

12. A sizing frame according to claim 11, wherein the sizing frame contains a sizing grid, and wherein, when the device is applied to the individual, the facial features and applied markings can be observed through the grid.

13. A system for selection of an appropriately sized therapy device for positioning on the external anatomy of the individual, comprising a plurality of sizing frames according to claim 1, each of the plurality of sizing frames corresponding to a different sized therapy device.

14. A method of fitting a therapy device, the therapy device configured to mate to an individual at a position corresponding approximately to the anterior triangle of the neck of the individual to create an enclosed space for the administration of negative pressure upon the external neck surface of the individual, comprising:
　　mating a sizing frame according to claim 1 to the patient at a skin surface of the individual corresponding to the contact surface of the therapy device; and
　　determining a goodness of fit of the sizing frame to the individual based on the mandible overlap, ear clearance dimension and mandible to neck angular relationship.

15. A method according to claim 14, wherein the determining step comprises determining whether the chamber gauge feature deviates from the skin surface of the upper airway of the individual by an amount of at least 1 cm, and if so, determining that the sizing frame provides a sufficient goodness of fit.

16. A method according to claim 14, wherein the determining step comprises determining whether the mating surface defines an effective therapy area of the individual's skin surface, and if so, determining that the sizing frame provides a sufficient goodness of fit.

17. A method according to claim 14, wherein the determining step comprises determining whether the mating surface minimizes mandible overlap, and if so, determining that the sizing frame provides a sufficient goodness of fit.

18. A method according to claim 14, wherein the determining step comprises determining whether the chamber gauge feature deviates from the skin surface of the upper airway of the individual by an amount of at least 1 cm, determining whether the mating surface defines an effective therapy area of the individual's skin surface, and determining whether the mating surface minimizes mandible overlap.

19. A method according to claim 14, wherein the method comprises mating a plurality of sizing frame according to to the patient at a surface of the individual corresponding to the contact surface of the therapy device, and determining which sizing frame in the plurality maximizes the goodness of fit to the individual.

* * * * *